US006148147A

United States Patent [19]

Durham

[11] Patent Number: 6,148,147

[45] Date of Patent: Nov. 14, 2000

[54] RESIN SUPPLY HOSE WITH REMOVABLE CORE

[75] Inventor: Mike D. Durham, Ventura, Calif.

[73] Assignee: Northrop Grumman Corporation, Los Angeles, Calif.

[21] Appl. No.: 09/148,286

[22] Filed: Sep. 4, 1998

[51] Int. Cl.[7] .......... A61F 7/00; H05B 3/40

[52] U.S. Cl. .......... 392/470; 392/465; 392/478

[58] Field of Search .......... 392/470, 465, 392/472, 478; 138/124, DIG. 1; 174/47; 222/146.2, 146.6

[56] References Cited

U.S. PATENT DOCUMENTS

| | | | |
|---|---|---|---|
| 2,758,194 | 8/1956 | Heron | 219/46 |
| 3,522,413 | 8/1970 | Chrow | 219/301 |
| 3,791,415 | 2/1974 | Lawless et al. | 138/127 |
| 4,038,519 | 7/1977 | Foucras | 219/301 |
| 4,352,007 | 9/1982 | Baker et al. | 219/301 |
| 4,447,707 | 5/1984 | Baker | 219/301 |
| 4,455,474 | 6/1984 | Jameson et al. | 219/301 |
| 4,467,837 | 8/1984 | Baker | 138/119 |
| 4,553,023 | 11/1985 | Jameson et al. | 219/301 |
| 4,644,134 | 2/1987 | Baker | 219/301 |
| 4,667,084 | 5/1987 | Regge | 219/301 |
| 5,093,896 | 3/1992 | Moore et al. | 392/441 |
| 5,428,706 | 6/1995 | Lequeux | 392/472 |
| 5,531,357 | 7/1996 | Guilmette | 222/1 |
| 5,667,142 | 9/1997 | Newman | 239/346 |
| 6,049,658 | 4/2000 | Schave et al. | 392/472 |

*Primary Examiner*—Teresa Walberg
*Assistant Examiner*—Thor Campbell
*Attorney, Agent, or Firm*—Terry J. Anderson; Karl J. Hoch, Jr.

[57] ABSTRACT

A heated resin supply hose for supplying molten resin in a molding process, such as a RTM process, includes a removable inner core tube or conduit that can be readily removed from reusable supply hose components after each injection cycle to make a molded article. The reusable hose components include a core-receiving conduit for slidably receiving the core conduit and a heating element on the core-receiving conduit as well as additional hose component layers. The used core conduit having residual resin therein is removed from the core-receiving conduit and replaced by a new core conduit that is inserted in the core-receiving conduit in making another molded article.

11 Claims, 2 Drawing Sheets

RESIN SUPPLY HOSE WITH REMOVABLE CORE

FIELD OF THE INVENTION

The present invention relates to a heated supply hose for supplying a molten material, such as molten resin, from a source to a mold or other resin using apparatus.

BACKGROUND OF THE INVENTION

In practicing the known resin transfer molding process (RTM process), a catalyzed resin, such as catalyzed epoxy resin, is melted in a heated, gas pressurized pot and supplied through a heated resin supply hose or pipe to a mold for infiltrating a fiber reinforcement positioned in the mold to form a fiber reinforced molded product. The resin supply hose or pipe is comprised of copper line with wrapped heating element. The hose components are fixed at opposite ends to conventional compression fittings that connect to tapped holes on the resin pot and the mold.

The heated resin supply hose previously used has been quite disadvantageous in the RTM injection molding of medium to high viscosity catalyzed epoxy resin wherein residual resin remains in the hose following each injection cycle. As a result, the supply hose must be cleaned with a suitable, environmentally hazardous solvent following each injection cycle in attempt to remove the residual resin, which may be partially or fully cured in the hose. The solvent is pumped through the supply hose to remove as much resin as possible. Despite these attempts to remove residual resin from the supply hose, there is experienced in practice of the RTM process a progressive build-up of residual resin in the supply hose that eventually requires the hose to be scrapped in toto and replaced by a new resin supply hose. Such detrimental resin buildup has been observed to occur in relatively short time, such as in as few as one injection cycle of the RTM process.

An object of the present invention is to provide a heated supply hose and method for supplying molten resin and other molten materials in a molding or other process that overcomes the aforementioned disadvantages.

SUMMARY OF THE INVENTION

The present invention provides a heated supply hose for supplying molten resin and other molten materials in a molding or other process that includes a removable inner core conduit that can be readily removed from the supply hose for disposal or cleaning and replaced by another removable inner core conduit such that the remaining hose components are reusable with the new core conduit.

In one embodiment of the present invention for supplying molten resin, a resin supply hose comprises a removable inner core tube or conduit made of material that can withstand the temperature and pressure of the molten resin. The removable core tube or conduit is slidable within reusable hose components so as to be removable following an injection cycle and replaceable with a new inner core conduit. For example, the removable inner core conduit is slidably received in a reusable core-receiving conduit such that the core conduit can be inserted and removed from the core-receiving conduit, for example, by pushing or pulling the removable core conduit into/out of the core-receiving conduit. A heating element is disposed on the core-receiving conduit with thermocouples optionally being disposed proximate the core-receiving conduit for temperature monitoring and control purposes. A reinforcement, such as a braided wire reinforcement, preferably is disposed on the heating element and peferably suround by a thermal insulating tube or layer with a protective outer casing disposed on the thermal insulating layer.

The opposite ends of the reusable hose components are connected to respective hose couplings that are adapted to be connected to the resin source and to the mold to secure the reusable hose components thereto when the core conduit is connected to the resin source and the mold for transferring molten resin. The removable inner core conduit includes opposite ends that extend beyond ends of the couplings and are provided with suitable fittings for connection to the resin source and the mold to this end.

Following a resin injection cycle to form a molded article, a method embodiment of the present invention involves removing the hose couplings from the resin source and the mold. The removable inner core conduit then is disconnected from the fittings at the resin source and mold. The fitting at one of the removable core conduit then is removed, for example, by cutting off one end of the core conduit. Then, the other end of the removable core conduit bearing the remaining fitting is pulled so as to remove the core conduit from the reusable hose components. The end of a new core conduit sans fitting then is inserted into the reusable hose components by pushing it through the core-receiving conduit so that opposite ends of the core conduit extend beyond ends of the couplings. A fitting(s) then is/are attached to the newly inserted core conduit for reuse of the resin supply hose in forming the next molded article.

The present invention is advantageous in that the removable inner core conduit is the only hose component that is replaced after use. The reusable hose components are reusable with a new, replacement core conduit to make an additional molded article. Moreover, the need to clean the resin supply hose with hazardous solvents to remove residual resin build-up therein is eliminated in the practice of the present invention.

The above and other objects and advantages of the present invention will become more readily apparent to those skilled in the art from the following detailed description taken with the following drawings.

DETAILED DESCRIPTION OF THE INVENTION

The present invention provides a heated resin supply hose especially useful, although not limited, to supplying or transferring a molten resin material in a molding or other process. For example only, the resin supply hose of the present invention is useful in transferring medium to high viscosity catalyzed epoxy resin from a resin melting pot to a mold having a conventional fiber reinforcement preform (not shown) positioned therein in accordance with the known RTM (resin transfer molding) process where the resin infiltrates and encapsulates the preform to form a reinforced molded resinous article. The catalyzed resin may comprise a catalyzed epoxy with having a medium to high viscosity in the range of 500 to 3000 centipoise in the practice of such RTM process for purposes of illustration only and not limitation.

Figure 1:
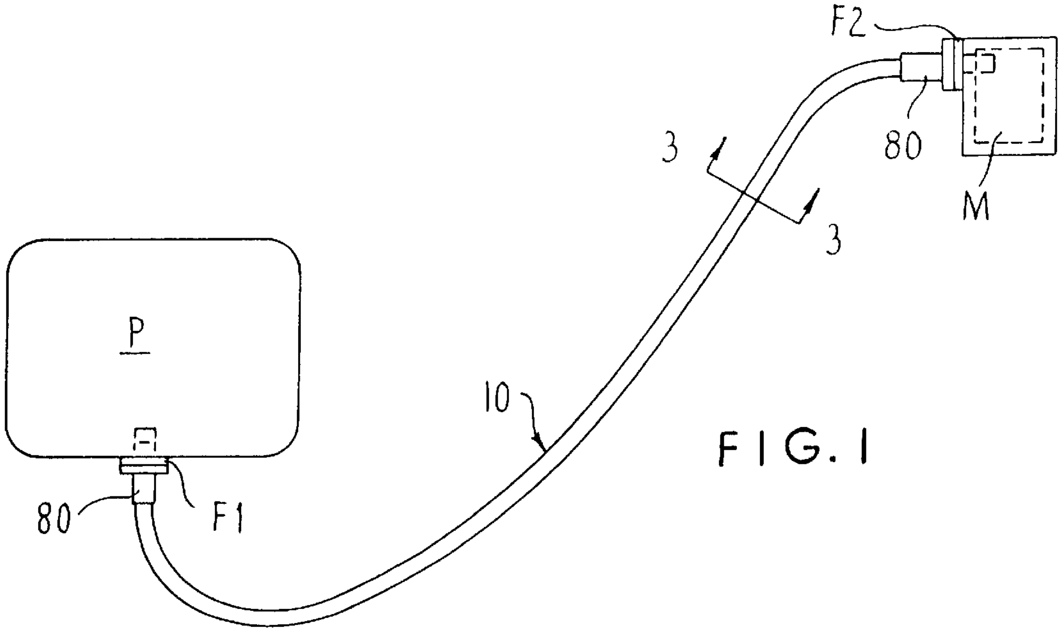
FIG. 1 is a schematic view of resin supply apparatus including a resin supply hose.
Figure 2:
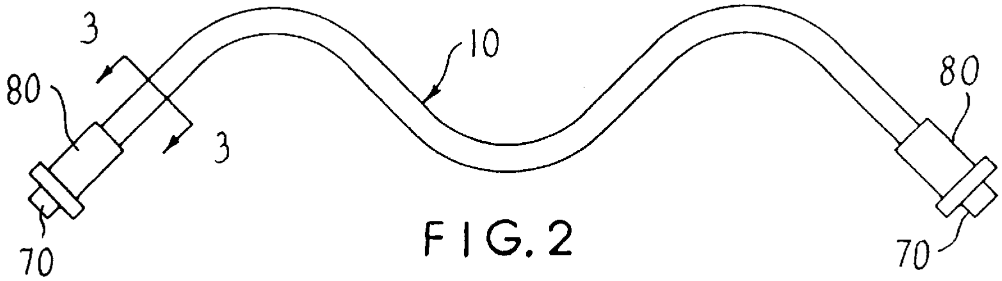
FIG. 2 is an elevational view of the resin supply hose pursuant to an embodiment of the invention.
Figure 3:
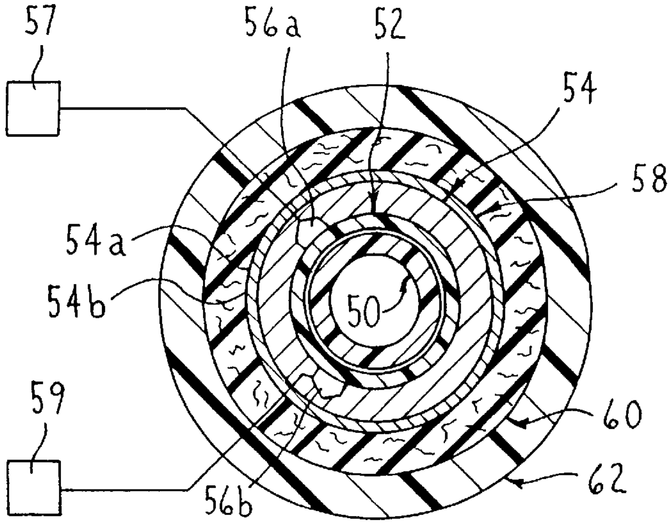
FIG. 3 is a sectional view of the resin supply hose along lines 3—3 of FIG. 2.
Figure 5B:
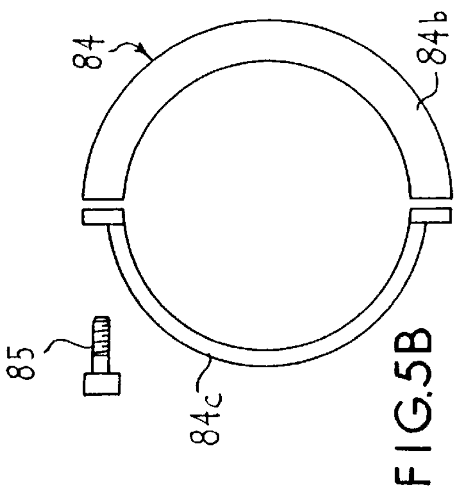
FIG. 5B is an exploded end elevation of the female hose coupling.
Figure 5A:
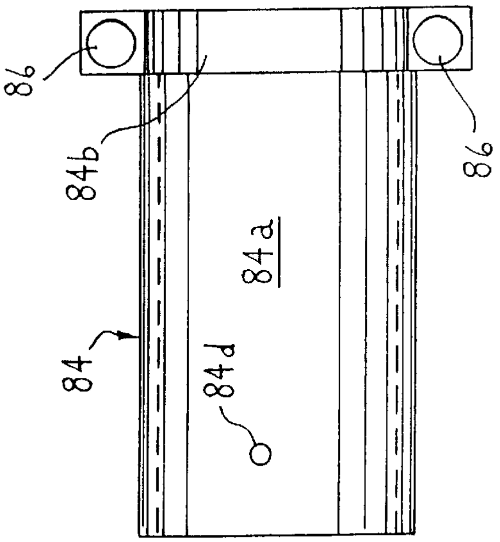
FIG. 5A is a side elevation of a female hose coupling.
Figure 4B:
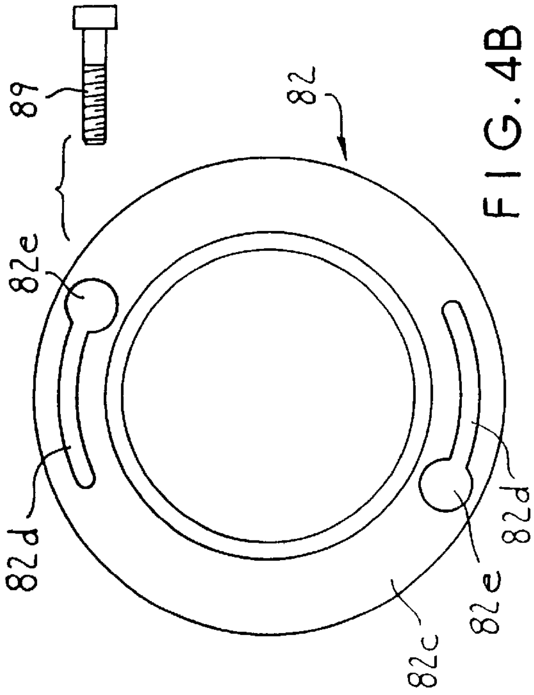
FIG. 4B is a end elevation of the male hose coupling.
Figure 4A:
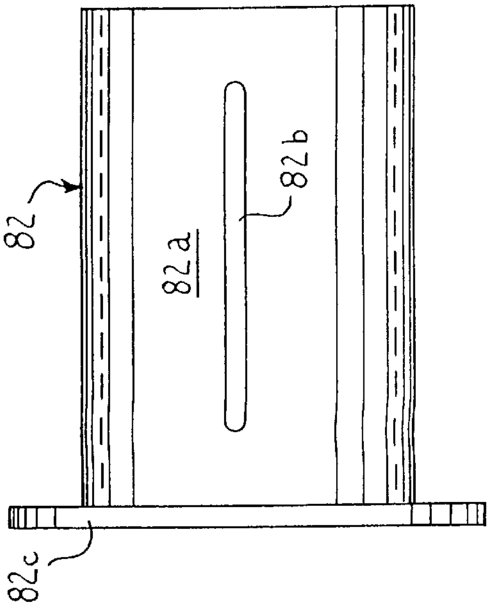
FIG. 4A is a side elevation of a male hose coupling.

Referring to FIGS. 1–3, a resin melting pot P is shown connected to a mold M by a heated, multi-layer resin supply hose 10. The molten resin is heated in the pot P to a molten resin state and forced by gas (air) pressure in the pot P through the flexible resin supply conduit 10 into the mold, which typically is evacuated to subambient pressure, to form the reinforced molded article.

The resin supply hose 10 comprises a removable inner core conduit 50 that can be readily removed from the supply hose for disposal or cleaning and replaced by a new removable inner core conduit such that the remaining hose components are reusable with the new inner core conduit 50. The inner core conduit 50 can comprise ⅜ inch outer diameter by 5⁄16 inch inner diameter commercially available Teflon TFE or PFA high temperature/high pressure cylindrical tubing that can withstand temperatures of −400 to +500 degrees F.

The length of the inner core conduit 50 is selected to connect the melting pot P and the mold M to transfer molten resin from the pot P to the mold M in practice of the RTM process. The opposite ends of the inner core conduit 50 are connected to the resin melting pot P and to the mold M by identical conventional compression fittings 70 on the ends of the core conduit. For example, ⅜ inch outer diameter by ¼ inch NPT (National Pipe Thread) brass compression fittings can be used on the opposite ends of the inner core conduit 50 to sealingly connect to complementary fittings (not shown) on the resin pot P and the mold M.

As mentioned above, the inner core conduit 50 is slidably received in the reusable hose components so as to be removable following an injection cycle and replaceable with a new inner core conduit. The reusable hose components comprise a reusable, relatively thin wall core-receiving conduit 52 having an inner diameter selected to slidably receive with small clearance or gap the removable inner core conduit 50. For example, the core-receiving conduit 52 can comprise ½ inch inner diameter high temperature Teflon cylindrical tubing to thereby provide a clearance or gap of 1⁄16 inch on radius between the core conduit 50 and the core-receiving conduit 52. The clearance or gap between the core conduit 50 and the core-receiving conduit 52 should be maintained at 1⁄16 inch or other appropriate dimension in order to provide adequate thermal conduction for heating of the resin in the supply hose as the molten resin is transferred from the pot P to the mold M.

The core-receiving conduit 52 can have an outer diameter of 9⁄16 inch, providing a wall thickness of 0.030 inch. The high temperature Teflon material of the core-receiving conduit 52 can comprise commercically avialable Teflon TFE tubing that can withstand temperatures of −400 to +500 degrees F.

A reusable heating element 54 is disposed on the core-receiving conduit 52. The heating element 54 can comprise a spiral wrapped nickel alloy electrical resistance heating element operable at 120 Volts AC and 10 Amperes to maintain 400 degrees F. temperature. A suitable heating element comprises a commercially available nickel-chromium heating element. The heating element is manually, spirally wrapped on the core-receiving conduit 52 in direct contact therewith to provide heating of the core conduit 50 and thus the molten resin transferred therethrough.

First and second thermocouples 56*a*, 56*b* typically are embedded against the outer wall of the core-receiving conduit 52. Thermocouple 56*a* monitors temperature and provides a signal representative of temperature to a conventional thermocouple temperature recorder 57 shown schematically in FIG. 3. Thermocouple 56*b* is a control thermocouple providing a similar signal to a conventional thermocouple controller 59 shown schematically. Controller 59 provides electrical current to the heating element 54 in response to the temperature sensed by thermocouple 56*b* in order to control the temperature at a preselected value, such as 280 degrees F. for molten catalyzed epoxy resin used in the RTM process. The heating element 54 includes wires 54*a*, 54*b* that extend to the controller 59 to this end. A third thermocouple (not shown) may be present as a back-up thermocouple in the event thermocouple 56*a* or 56*b* should fail in use.

A reusable reinforcement 58 is disposed on the heating element 54 to reinforce the supply hose against the resin injection pressure present in the inner core conduit 50 during the resin injection cycle. The resin pressure may be in the range of 20 to 150 psi for catalyzed epoxy resin in practice of the RTM process. The reinforcement 58 typically comprises a single layer braided stainless steel wire tubing disposed on the heating element 54.

The reinforcement 58 is surrounded by a reusable thermal insulating tube or wrap 60 having a reusable protective outer casing 62 disposed thereon. The thermal insulating tube or wrap 60 can comprise a fiberglass reinforced silcone rubber tubing having a wall thickness of approximately 0.25 inch.

The protective outer casing 62 can comprise an abrasion-resistant braided polyester outer casing having a wall thickness of about 0.050 inch.

The reusable hose components including the core-receiving conduit 52, heating element 54, thermal insulating tube 60, and protective outer casing 62 have a common length that is less than the length of the removable inner core conduit 50. The opposite ends of these reusable hose components are connected to respective reusable or non-reusable metal (e.g. brass) hose end couplings 80. Couplings 80 are adapted to be connected to the resin pot P and the mold M to secure the reusable hose components thereto when the inner core conduit 50 is connected by compression fittings 70 to the pot P and the mold M.

The couplings 80 are identical and include a male tubular hose coupling 82 and a female tubular hose coupling 84 as shown in FIGS. 4A, 4B and FIGS. 5A, 5B, respectively. The female hose coupling 84 includes tubular section 84*a* that receives the outermost ends of the reusable hose components and an inner end flange 84*b* and end clamp 84*c* mthat is fastened to the end flange 84*b* by screws 85 received in threaded holes 86 to clamp and hold the ends of the reusable hose components in the female coupling 84. The inner diameter (e.g. 3.4 inches) defined by the end flange 84*b* and clamp 84*c* when fastened together is less than the total outer diameter (e.g. 3.8 inches) of the reusable hose components such that the opposite hose ends are clamped in each female coupling 84. The inner diameter of the tubular section 84*a* of each female coupling 84 is approximately equal to the total outer diameter of the reusable hose components.

The tubular section 84*a* includes a press-fit pin 84*d* that projects radially outwardly. The pin 84*d* comprises a ⅛ inch diameter by 0.20 inch long pin press-fit in a hole machined in the tubular section 84*a*.

The male hose coupling 82 includes tubular section 82*a* that receives the tubular section 84*a* of the female coupling 84 in sliding fit or relation. The tubular section 82*a* includes an elnogated, axially extending slot 82*b* (e.g. 0.135 inch in width and 2.0 inches long) that receives the press-fit pin 84*d* of the female coupling 84 such that the pin 84*d* moves within the slot when the male and female couplings 82, 84 are relatively moved and retains the male and female couplings 82, 84 together.

The tubular section 82*a* of each male coupling 82 includes an outermost annular flange 82*c* that is adapted to engage a similar flange F1, F2 on the melting pot P and on the mold M, respectively. The flange 82*c* includes arcuate, relatively narrow (e.g. 0.26 inch width) slots 82*d* at opposite diametral regions for receiving the shafts of cap head screws 89 threaded into the aforementioned flanges at the resin pot P and the mold M. The slots 82*d* include enlarged regions 82*e* through which the heads of the screws 89 pass when the male coupling 82 is engaged to the flanges F1, F2 at the resin pot P and the mold M. After the screws 89 are received in the enlarged regions 82*e*, the male coupling 82 is rotated to position the shafts of the screws 89 in the narrow slot regions 82*d* so that the screw heads overlie the flange 82*c* and can be tighten thereagainst to fasten the coupling 80 to the flanges F1, F2 of resin pot P and the mold M.

The reusable hose components thereby are secured to the resin pot P and the mold M when the removable inner core conduit 50 is connected by the compression fittings 70 to the fittings of the resin pot P and the mold M in order to transfer molten resin from the pot P to the mold M during a typical RTM injection cycle to form a fiber reinforced molded article.

Following a typical injection cycle to form the fiber reinforced molded article, the couplings 80 are removed from the resin pot P and the mold M by untightening the screws 89 and rotating the male couplings 80 in a direction to align the screws 89 at the enlarged regions 82*e* of the slots 82*d*. The male couplings 80 then simply are pulled off the pot P and the mold M with the male coupling 82 sliding over the female coupling 84 as guided by the press-fit pin 84*d* in the slot 82*b*.

The compression fittings 70 then are disconnected from the fittings of the pot P and the mold M to disconnect the inner core conduit 50 therefrom. The resin supply hose or conduit 10 is now free from the pot P and mold M.

One of the fittings 70 at the end of the removable core conduit 50 then is removed, for example, by cutting off that end of the core conduit 50 extending beyond a coupling 80. Then, the other end of the removable core conduit 50 bearing the remaining fitting 70 is grasped and pulled so as to remove the core conduit 50 having residual resin therein from the reusable hose components. Of course, both ends of the used core conduit 50 can be cut off to remove both fittings 70, if desired, for removal of the inner core conduit 50 from the reusable hose components.

The end of a new replacement core conduit 50 sans fitting 70 at one or both ends then is inserted into the reusable hose components by pushing it through the core-receiving conduit 52 so that opposite ends of the core conduit 50 extend beyond the couplings 80, FIG. 1. A compression fitting 70 then is attached at one or both of the opposite ends, as needed, of the newly inserted core conduit 50 for reuse of the resin supply hose 10 in forming the next molded article.

In particular, the compression fittings 70 at the opposite ends of the replacement inner core conduit 50 are connected to the respective fittings at the pot P and the mold M. Then, the male couplings 80 are connected to the pot P and the mold M as described for conducting the next injection cycle.

The present invention is advantageous in that the removable inner core conduit is the only hose component that is replaced after use. The reusable hose components are reusable with new core conduits to make additional molded articles. Moreover, the need to clean the resin supply hose with hazardous solvents to remove residual resin build-up therein is eliminated in the practice of the present invention.

While the invention has been described with respect to certain specific embodiments thereof for purposes of illustration and not limitation, those skilled in the art will appreciate that the invention envisions that modifications, changes, and the like can be made therein without departing from the spirit and scope of the invention as set forth in the appended claims.

I claim:

1. A supply hose for molten material, comprising a removable inner core conduit for transferring the molten material and slidably received in reusable hose components that include a core-receiving conduit and a heating element disposed proximate said core-receiving conduit.

2. The hose of claim 1 further including a reinforcement disposed on said heating element.

3. The hose of claim 2 wherein the reinforement comprises a braided metal wire reinforcement disposed about the core-receiving conduit.

4. The hose of claim 2 further including a thermal insulation disposed about the reinforcement and a protective outer casing disposed about the thermal insulation.

5. The hose of claim 1 further including first and second thermocouples disposed proximate the core-receiving conduit for temperature monitoring and control purposes.

6. The hose of claim 1 wherein the opposite ends of the reusable hose components are connected to respective couplings.

7. The hose of claim 6 wherein the core conduit includes opposite ends that extend beyond the couplings and are provided with a respective fitting for connection to a resin source and a mold so that molten resin can be supplied from the source to the mold.

8. The hose of claim 7 wherein said couplings each include a female coupling clamped on the supply hose and a male coupling movably received in the female coupling.

9. A resin supply hose for molten resin, comprising a removable inner core conduit for transferring the molten material and reusable hose components comprising a core-receiving conduit for receiving said core conduit for sliding movement therein, a heating element disposed on said core-receiving conduit, a reinforcement disposed on said heating element, a thermal insulating layer disposed on the reinforcement, and a protective outer casing disposed on the thermal insulating layer, said core conduit including opposite ends that extend beyond ends of said core-receiving conduit and provided with a respective fitting for connection to a resin source and a mold so that molten resin can be supplied from the source to the mold.

10. The hose of claim 9 wherein said reusable hose components include opposite ends that are connected to respective couplings.

11. The hose of claim 10 wherein the core conduit includes opposite ends that extend beyond the couplings and are provided with a respective fitting for connection to the resin source and the mold so that molten resin can be supplied from the source to the mold.

* * * * *